(12) United States Patent
Boumediene et al.

(10) Patent No.: US 7,449,487 B2
(45) Date of Patent: Nov. 11, 2008

(54) USE OF UNSAPONIFIABLE COMPONENTS OF VEGETABLE OILS FOR PREPARING A COSMETIC AND RELATED TREATMENTS

(75) Inventors: Karim Boumediene, Ussy (FR); Jean-Pierre Pujol, Douvres-la-Delivrande (FR); Georges Bernard Guillou, La Chapelle-sur-Erdre (FR); Philippe Msika, Paris (FR); Chafik Ghayor, Caen (FR)

(73) Assignee: Laboratoires Expanscience, Courbevoie Cedex (FR)

( * ) Notice: Subject to any disclaimer, the term of this patent is extended or adjusted under 35 U.S.C. 154(b) by 610 days.

(21) Appl. No.: 10/619,686

(22) Filed: Jul. 15, 2003

(65) Prior Publication Data

US 2004/0018257 A1 Jan. 29, 2004

Related U.S. Application Data

(62) Division of application No. 09/868,989, filed as application No. PCT/FR99/03272 on Dec. 23, 1999, now abandoned.

(30) Foreign Application Priority Data

Dec. 23, 1998 (FR) .................................. 98 16328

(51) Int. Cl.
*A61K 31/42* (2006.01)
(52) U.S. Cl. ...................................................... 514/379
(58) Field of Classification Search ................... 424/95, 424/107, 364, 59, 64, 237
See application file for complete search history.

(56) References Cited

U.S. PATENT DOCUMENTS

| | | | |
|---|---|---|---|
| 3,993,756 A | 11/1976 | Kaneda et al. | |
| 4,386,067 A * | 5/1983 | Guillon | 424/522 |
| 5,262,163 A | 11/1993 | Rancurel | |
| 5,498,411 A * | 3/1996 | Rancurel | 426/417 |
| 5,627,289 A | 5/1997 | Jeromin | |
| 5,741,496 A | 4/1998 | Khaiat | |
| 5,998,396 A | 12/1999 | Nakano | |
| 6,146,616 A | 11/2000 | Msika | |
| 6,190,689 B1 | 2/2001 | Hoffmann et al. | |

FOREIGN PATENT DOCUMENTS

| | | |
|---|---|---|
| CA | 2132369 | 3/1995 |
| EP | 0 643 980 | 3/1995 |
| FR | 2 231 394 | 12/1974 |
| FR | 2 678 632 | 1/1993 |
| FR | 2 762 512 | 10/1998 |
| GB | 1 427 253 | 3/1976 |

OTHER PUBLICATIONS

Helen Kim et al.; "Mechanisms of Action of the Soy Isoflavone Genistein: Emerging Role for its Effects Via Transforming Growth Factor-β Signaling Pathways 1-3", The American Journal of Clinical Nutrition, vol. 68, No. 6, (suppl), pp. 1418S-1425S, © 1998 American Society for Clinical Nutrition.
Par H. Thiers et al., "Un Groupe D'Agents Therapeutiques Noveaux: Les Insaponifiables Des Huiles Vegetables, Leurs Carotenoids, Leurs Indetermines Administres En Solution Alcoolique", Therapie, vol 16, pp. 235-251, 1961, no translation.
Maheu et al., "Symptomatic efficacy of avocado/soybean unsaponifiables in the treatment of osteoarthritis of the knee and hip," Arthritis & Rheumatism, Jan. 1998, 41(1):81-91.
Woolf et al., "Burden of major musculoskeletal conditions," Bulletin of the World Health Organization, 2003, 81(9):646-656.
International Search Report for PCT/FR99/03272, dated May 16, 2000.
Vidal, Piasciedine 300, 1995, 3 pgs. with English translation.
Farines et al., "Influence of Avocado Oil Processing on the Nature of Some Unsaponifiable Constituents." JAOCS, 1995, 72(4). 473-476.

* cited by examiner

*Primary Examiner*—Raymond J Henley, III
(74) *Attorney, Agent, or Firm*—Foley & Lardner LLP

(57) ABSTRACT

The invention relates to the use of at least one unsaponifiable component of vegetable oil, in particular of avocado, soya bean and/or lupin oils, for the preparation of a medicament intended to stimulate the expression of TGF-β or the expression of the plasminogen activator inhibitor PAI-1.

The invention also relates to a method of cosmetic treatment comprising the application of at least one unsaponifiable component of vegetable oil as well as the use of the latter as additive in a food for human beings and/or for animals.

17 Claims, 7 Drawing Sheets

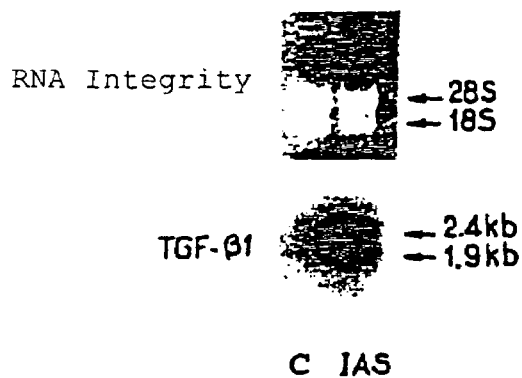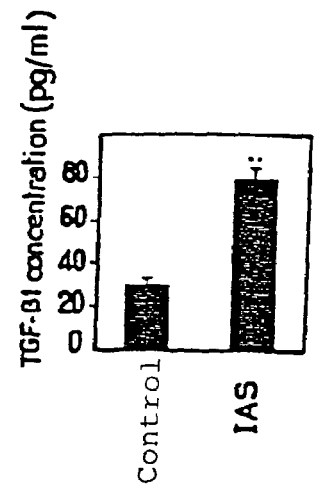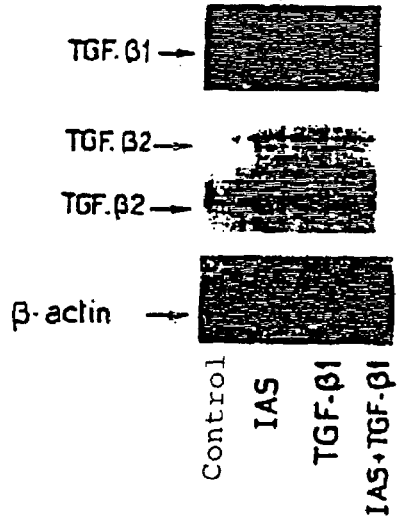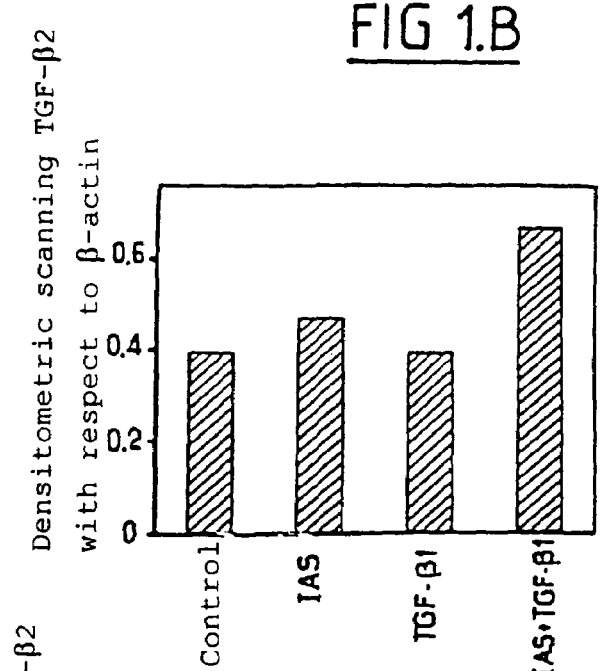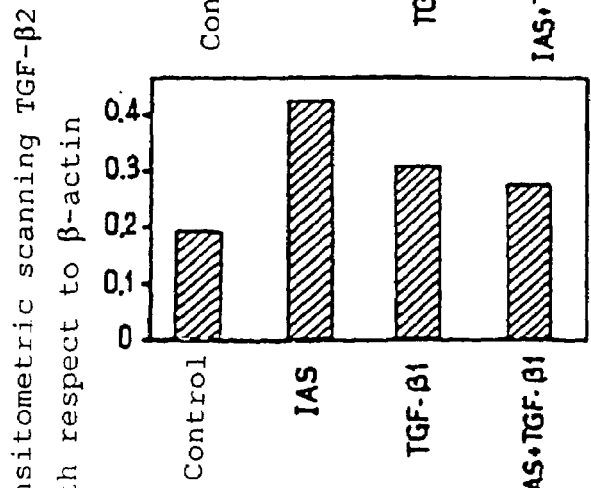
FIG 1.A
FIG 1.B
FIG 2A
FIG 2.B

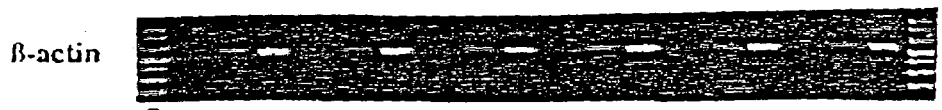
FIG.3A
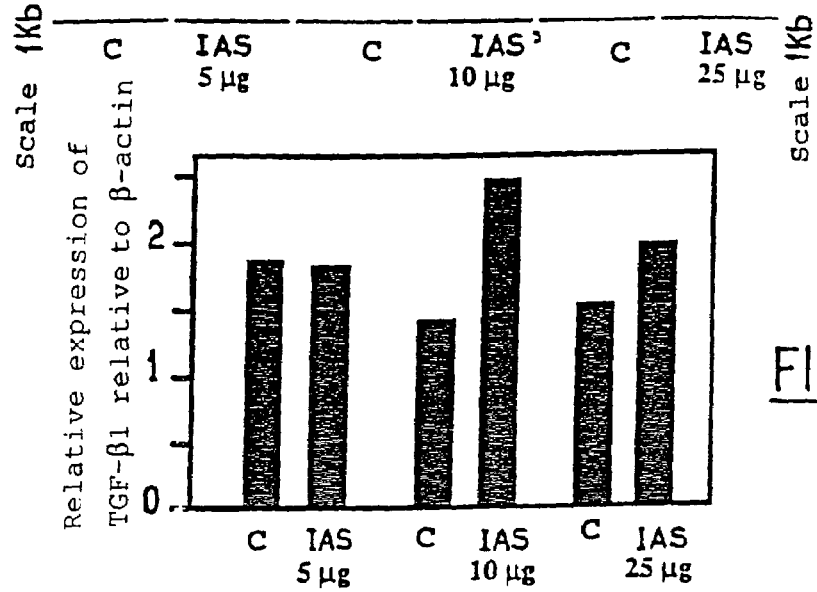
FIG.3B
FIG.3C
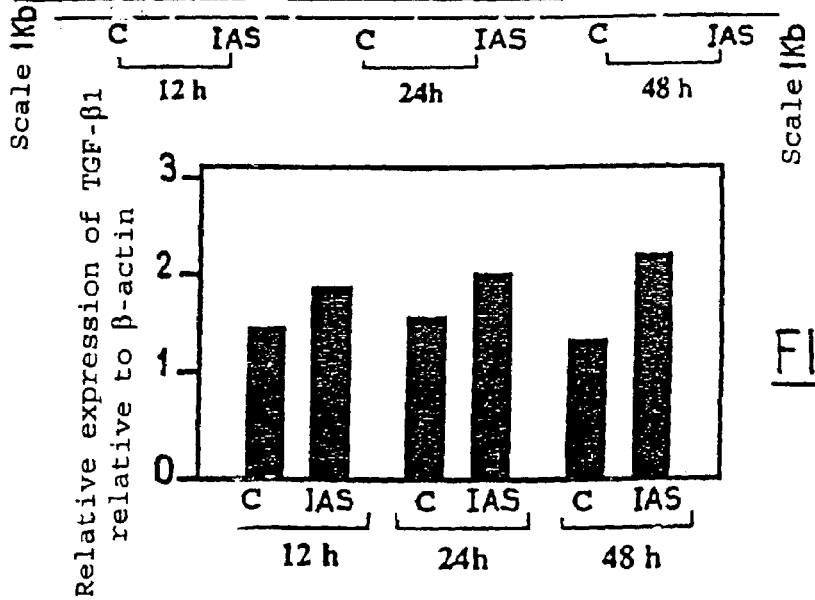
FIG.3D

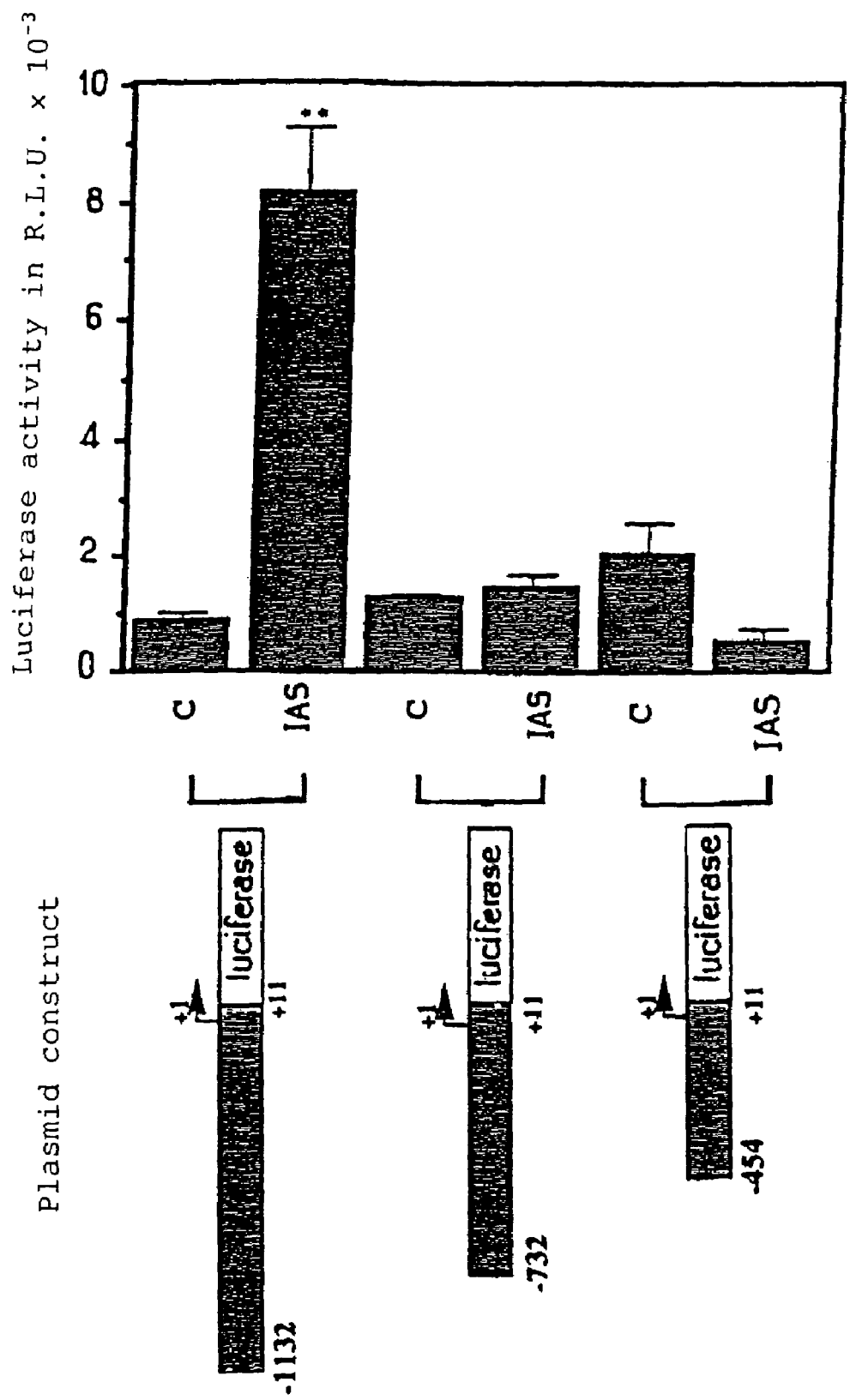
FIG_4

TβR I
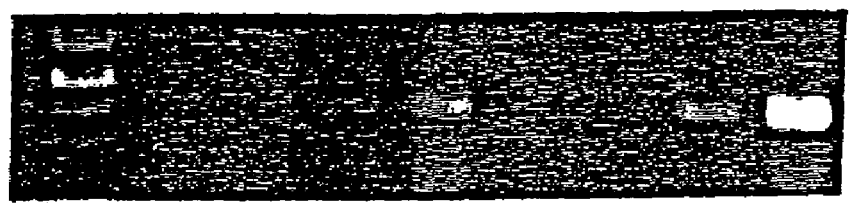
TβR II
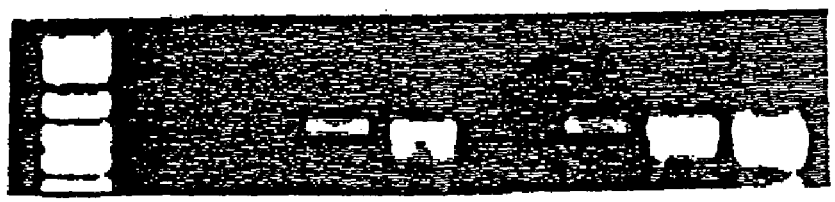
β-actin
FIG_5

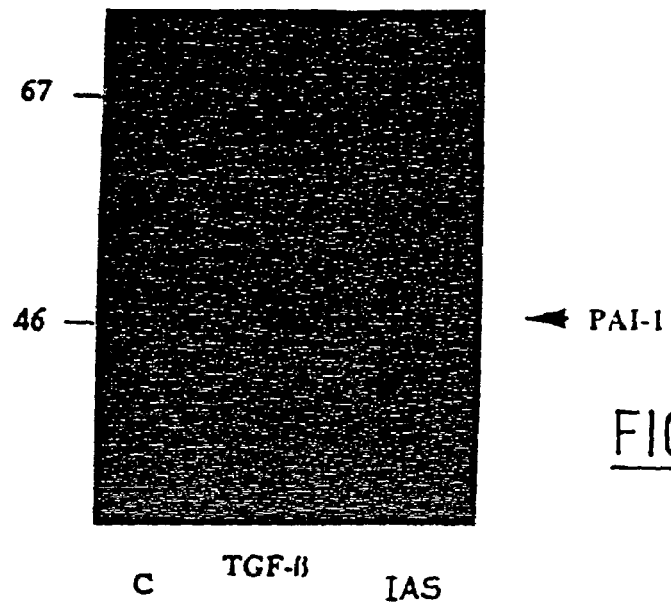
FIG_6A
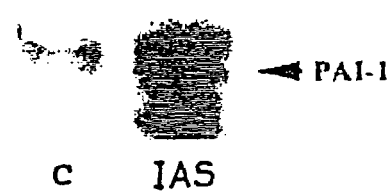
FIG_6B
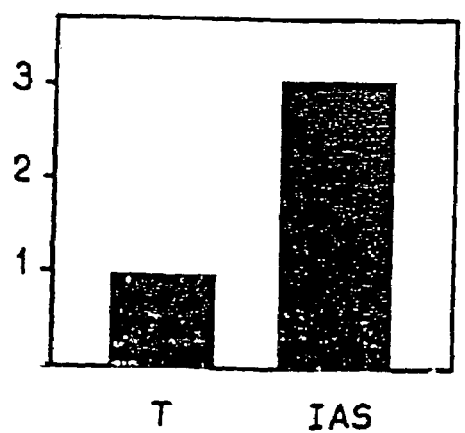
FIG_6C

*: p<0.05; **: p<0.01

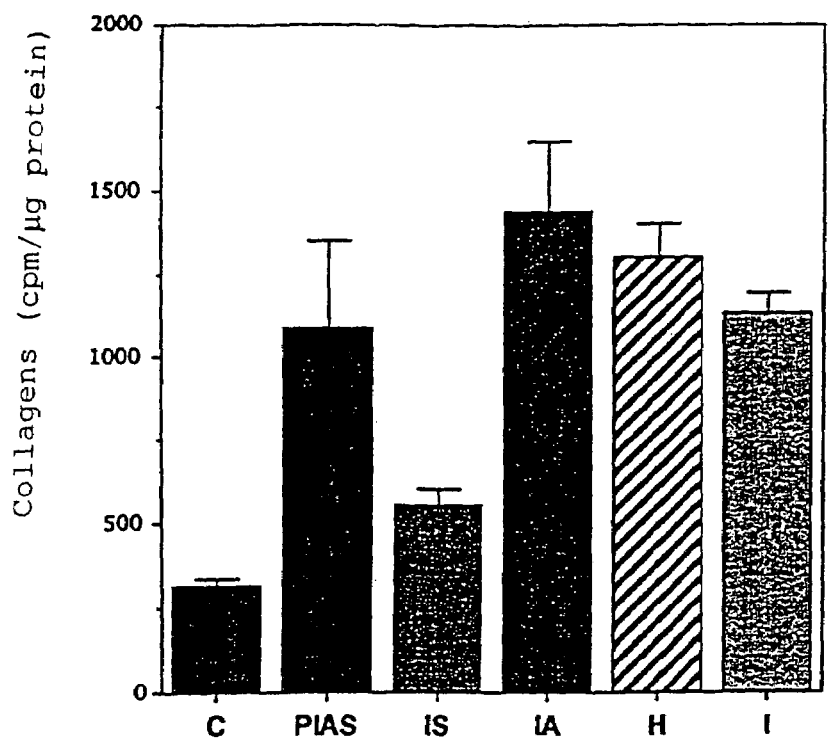
FIG 8.A
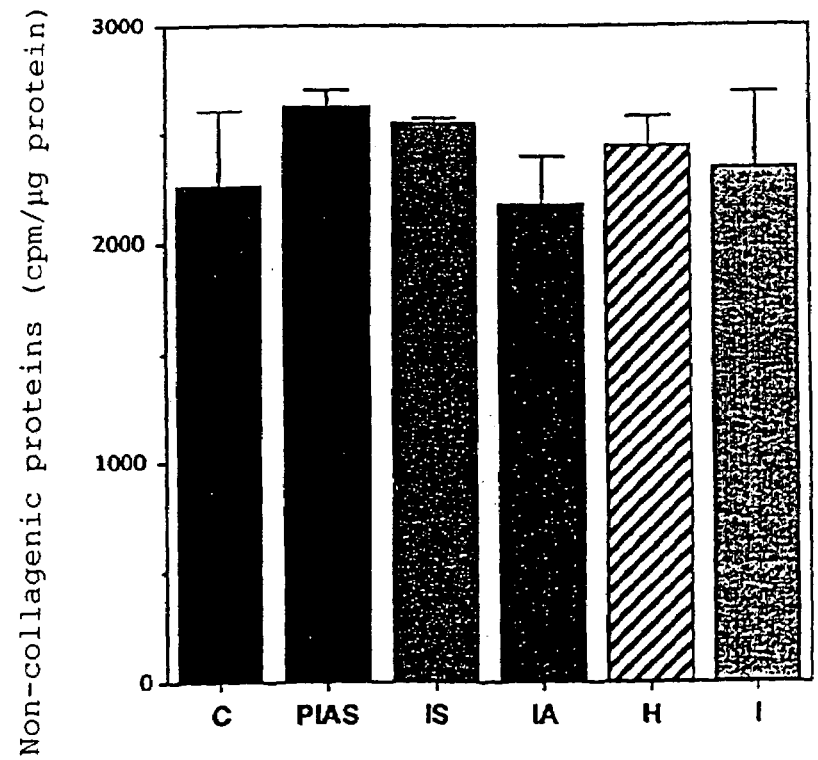
FIG 8.B

USE OF UNSAPONIFIABLE COMPONENTS OF VEGETABLE OILS FOR PREPARING A COSMETIC AND RELATED TREATMENTS

CROSS REFERENCE TO RELATED APPLICATIONS

This application is a division of application Ser. No. 09/868,989, filed Jun. 22, 2001 and assigned a filing date under 35 U.S.C. § 371 on Oct. 2, 2001, which is the National Stage of International Application No. PCT/FR99/03272, filed Dec. 23, 1999, which claims priority to French Application No. 98/16328, filed Dec. 23, 1998, application Ser. No. 09/868,989 is incorporated herein by reference in its entirety.

BACKGROUND

The present invention relates to the use of the unsaponifiable components of vegetable oils, in particular of avocado, soya bean and/or lupin oils, for the preparation of a medicament stimulating the expression of TGF-β or the expression of the plasminogen activator inhibitor PAT-1, as well as a method of cosmetic treatment according to which a composition based on unsaponifiable component of vegetable oils is applied to the skin, the neighbouring mucous membranes and/or the superficial body growths.

"TGF-β" is understood to mean, according to the invention, the different isoforms of TGF-β, that is to say the isoforms of the transforming growth factor β. The isoforms of TGF-β constitute a family of homodimeric polypeptides having a molecular weight of about 25 kD. Among the 5 known isoforms, the best characterized are the TGF-β1 and TGF-β2 (Sporn et al. (1987), J. Cell Biol. 105, 1039-1045; Roberts and Sporn (1990), Handbook of Exp. Pharmacol. 35, 419-472, Springer Verlag, Heidelberg). Although these two isoforms exhibit only 71% homology, they appear to have many activities in common. TGF-β1 was first isolated from human platelets, but it is now known that the majority of cells are capable of expressing it. TGF-β2 was purified from platelets, from bovine bone and from glioblastoma cells.

It is known that TGF-β is involved in complex mechanisms of progression of various pathologies and that it is desirable to reinforce the action of TGF-β, in other words to increase its expression by the very cells involved in the mechanisms of the said pathologies, for a favourable progression of the latter.

Thus, for example, it is known that the TGF-β expressed by the articular chondrocytes is involved in anabolic mechanisms of reaction, that is to say of restoration, of the articular cartilage which are observed at the first stages of osteoarthritis and which tend to compensate for the degradation of the cartilage resulting from the activity of metallo-proteases which are excessively secreted by the chondrocytes under the effect of cytokines, such as interleukin-1 (IL-1). It would therefore be desirable, for example in the case of osteoarthritis, to slow down the progression of this disease not only by blocking the activity of interleukin-1 by known means but also by promoting the expression of TGF-β.

Moreover, it is known that TGF-β is favourably involved in the mechanisms of bone remodelling which occur during osteoporosis. This has been shown in particular by Boyce et al. of the University of Texas ((1996), Nature Med. (2), 10, 1132-1136).

Finally, TGF-β also plays a favourable role in some mechanisms of differentiation of nerve cells which are induced by the nerve growth factor (NGF or "nerve growth factor") as well as in many aspects of tissue, in particular skin, repair.

Taking into account the preceding text, it was therefore highly desirable to be able to obtain a stimulatory effect on the expression of TGF-β, in particular in order to improve the treatment of the pathologies described above.

Moreover, "plasminogen activator inhibitor 25 PAI-1" is understood to mean, according to the invention, the specific inhibitor PAI-1 which, with the other inhibitor PAI-2, regulates, in a known manner, the activity of the tissue form (tPA) and of the urokinase type (uPA) of the plasminogen activator PA. The two forms of PA, tPA and uPA, are produced by two different genes and have different molecular weights and immunological reactivity (Dano et al., (1985) Adv. Cancer Res. 44, 139-166; Hart et al., (1988), Comp. Bioch. Physiol. 90 B, 691-708). The inhibitors PAI-1 and PAI-2 form stable complexes with tPA and uPA. PAI-1 is the form which is predominant in the plasma and is produced by the endothelial cells, the platelets and the cells of the joint such as the synovial cells and the chondrocytes (Hart et al., 1988; Campbell et al., 1991; Hamilton et al., 1992).

It would be particularly advantageous to be able to stimulate the expression of the plasminogen activator inhibitor PAI-1 since an inhibition of the action of the metalloproteases and therefore, in particular, a contribution to the action of TGF-β for a favourable progression of the abovementioned pathologies would thus be obtained.

SUMMARY

It has now been observed, quite surprisingly and unexpectedly, that the use of unsaponifiable components of vegetable oil makes it possible to obtain not only a stimulatory effect on the expression of TCF-β but also a stimulatory effect on the expression of plasminogen activator inhibitor PAI-1.

Thus, the present invention relates to the use of at least one unsaponifiable component of vegetable oil for the preparation of a medicament intended to stimulate the expression of TGF-β or the expression of the plasminogen activator inhibitor PAI-1.

In particular, the use according to the invention is characterized in that the medicament is intended to stimulate the expression of TGF-β, and more particularly the expression of the isoforms TGF-β1 and TGF-β2.

More particularly, as is clearly evident from Example 1 below, the use according to the invention is characterized in that the medicament is intended to stimulate the expression of TGF-β via the DNA sequences situated between −1132 and −732 base pairs (bp) of the promoter of TGF-β and in particular of the promoter of the isoform TGF-β1.

The use according to the invention is also characterized in that the medicament is intended to stimulate the expression of the plasminogen activator inhibitor PAI-1.

In general, the unsaponifiable component is the fraction of a fatty substance which, after prolonged action of an alkaline base, remains insoluble in water and may be extracted with an organic solvent. Five main groups of substances are present in the majority of the unsaponifiable components of vegetable oils: saturated or unsaturated hydrocarbons, aliphatic or terpenic alcohols, sterols (or "phytosterols"), tocopherols and tocotrienols, the carotenoid and xanthophillic pigments.

Preferably, the unsaponifiable component of vegetable oil used according to the invention is chosen from the group consisting of the unsaponifiable component of avocado oil, the unsaponifiable component of soya bean oil, the unsaponifiable component of lupin oil and mixtures of the latter.

Comparison of the contents of unsaponifiable components of different vegetable oils: soya bean, cotton, coconut, olive and avocado shows a very high level of unsaponifiable component of the avocado oil obtained by extraction according to various known processes. Typically, the contents obtained range from 2 to 7% of unsaponifiable component in avocado oil against 0.5% in coconut oil, 1% in soya bean oil, 1% in olive oil.

The higher content of unsaponifiable component in avocado oil compared with the other vegetable oils such as those mentioned above can be explained in particular by the presence, in the unsaponifiable component of avocado oil, of constituents which are not generally found in the unsaponifiable component of many other vegetable oils such as furan compounds and polyhydroxylated fatty alcohols and which, on their own, represent more than 50% of the unsaponifiable component. The products specific to this unsaponifiable component of avocado may be divided into two chemical fractions called "fraction I" and "fraction H". The active compounds for use according to the invention are present in fraction H and its precursors. Fraction H is first to appear on a gas chromatograph of the unsaponifiable component of avocado oil.

The unsaponifiable component of avocado oil used according to the invention may be obtained from fresh fruit but, preferably, the unsaponifiable component of avocado oil used according to the invention is the unsaponifiable component of dry-avocado oil (that is to say the unsaponifiable component obtained from the oil of the dry avocado fruit).

According to the invention, the unsaponifiable component of avocado preferably comprises at least its fraction enriched with furan derivatives (fraction H), its fraction enriched with polyhydroxylated fatty alcohols (fraction I) or a mixture of these fractions.

As regards the unsaponifiable component of soya bean oil, it may be noted that this unsaponifiable component is mainly composed of sterols (40 to 65%) and of tocopherols ($\geq 10\%$). The principal sterols are β-sitosterol (40 to 70% of the total sterols), campesterol (15 to 30% of the total sterols) and stigmasterol (10 to 25% of the total sterols). The tocopherols are present in the form of a mixture of α-tocopherol (5 to 35% of the total tocopherols), γ-tocopherol (45 to 70% of the total tocopherols) and δ-tocopherol (10 to 43% of the total tocopherols).

The lupin oil may be extracted from lupin 25 flours and/or seeds.

Lupin is a close relative of the pea, of the broad bean, of the soya bean and of the french bean. The seed is traditionally used for human consumption for its high protein content. It is also incorporated into the feed for ruminants in the form of the whole plant or of its seeds and is also frequently used as green manure. More particularly, four species of lupin are of real agroriomic interest: white lupin (lupinus albus), blue lupin (lupinus angustifolius), yellow lupin (lupinus luteus) and South American lupin (lupinus mutabilis).

It was observed that lupin oil has a particularly high content of tocopherol, carotene (in particular β-carotene) and polyphenolic derivatives.

According to the invention, it is also preferable to use any unsaponifiable component of vegetable oil containing fractions rich in phytosterols, tocopherols, tocotrienols, terpenic and triterpenic hydrocarbons, natural antioxidants, in particular the unsaponifiable component of canola, rapeseed, sunflower, palm, maize, sesame and wheatgerm oil, the unsaponifiable component of soya bean oil, and mixtures of the latter. Persons skilled in the art can easily understand that the term "rich" refers to contents of these various components respectively cited which are above the respective average contents obtained considering all the vegetable oils known to persons skilled in the art.

BRIEF DESCRIPTION OF THE FIGURES

FIG. 1 (that is to say FIGS. 1.A and 1.B) represents a photograph of a northern-blot experiment (FIG. 1.A) showing the enhanced expression of the mRNA for TGF-β in the cells treated with the unsaponifiable components of avocado and of soya bean (Piasclédine 300®; designated by the reference "IAS" in FIGS. 1 to 6) as well as a histogram (FIG. 1.B) corresponding to a protein assay showing the enhanced protein expression of TGF-β1 in the cells treated with Piasclédine 300® (the control is designated by the reference "C" in FIGS. 1 to 6).

FIG. 2 (that is to say FIGS. 2.A and 2.B) shows the effects of the unsaponifiable components of avocado and of soya bean alone, of TGF-β1 alone and of the combination [unsaponifiable components of avocado and of soya bean and TGF-β1] on the expression of the mRNAs for the isoforms TGF-β1 and TGF-β2 as explained at the end of Example 1 below, paragraph 2.1. In particular, the northern-blot photographs (FIG. 2.A) show the expression of the mRNA for TGF-β1, TGF-β2 and for β action taken as control. The results of the expression of the mRNAs for the isoforms TGF-β1 and TGF-β2, respectively, are represented in the form of the respective histograms (FIG. 2.B).

FIG. 3 (that is to say FIGS. 3.A, 3.B, 3.C and 3.D) illustrates the effects, over time and according to the doses used of the unsaponifiable components of avocado and of soya bean (Piasclédine 300® on the expression of TGF-β1. FIG. 3.A is a photograph of an electrophoresis gel of RT-PCR amplification product from mRNA for TGF-β1 of cells treated with different quantities of unsaponifiable components of avocado and of soya bean (Piasclédine 300®). The results are normalized and expressed in histogram form (FIG. 3.B). FIG. 3.C is a photograph of an electrophoresis gel of RT-PCR amplification product from mRNA for TGF-β1 of cells treated at various times with the unsaponifiable components of avocado and of soya bean (Piasclédine 3000®). The results are normalized and expressed in histogram form (FIG. 3.D).

FIG. 4 shows the effects of the unsaponifiable components of avocado and of soya bean (Piasclédine 300®) on the expression of luciferase as a function of various TGF-β1 promoter constructs.

FIG. 5 is a photograph of an electrophoresis gel of RT-PCR amplification product from mRNA for TGF-β1 and TGF-β2 receptors and from mRNA for β-actin taken as control, obtained from cells treated with the unsaponifiable components of avocado and of soya bean (Piasclédine 300®).

FIG. 6 (that is to say FIGS. 6.A, 6.B and 6.C) illustrates the effect of the unsaponifiable components of avocado and of soya bean (Piasclédine 300®) on the expression of the plasminogen activator inhibitor PAI-1. FIG. 6.A represents a photograph of an electrophoresis gel of protein obtained by extraction from cells treated with Piasclédine 300® or TGF-β. FIG. 6.B is a northern-blot photograph showing the expression of RNA for PAI-1 in the cells treated with Piasclédine 300®. The results of the northern-blot experiment are normalized and expressed in histogram form in FIG. 6.C.

FIG. 8 (that is to say FIGS. 8A and 8B) shows the effect of the unsaponifiable components of avocado and of soya bean and of fractions H and I on the biosynthesis of collagen (FIG. 8A) and of noncollagenic proteins (FIG. 8B), by dermal fibroblasts in culture.

DETAILED DESCRIPTION OF THE PREFERRED EMBODIMENTS

Figure 7:
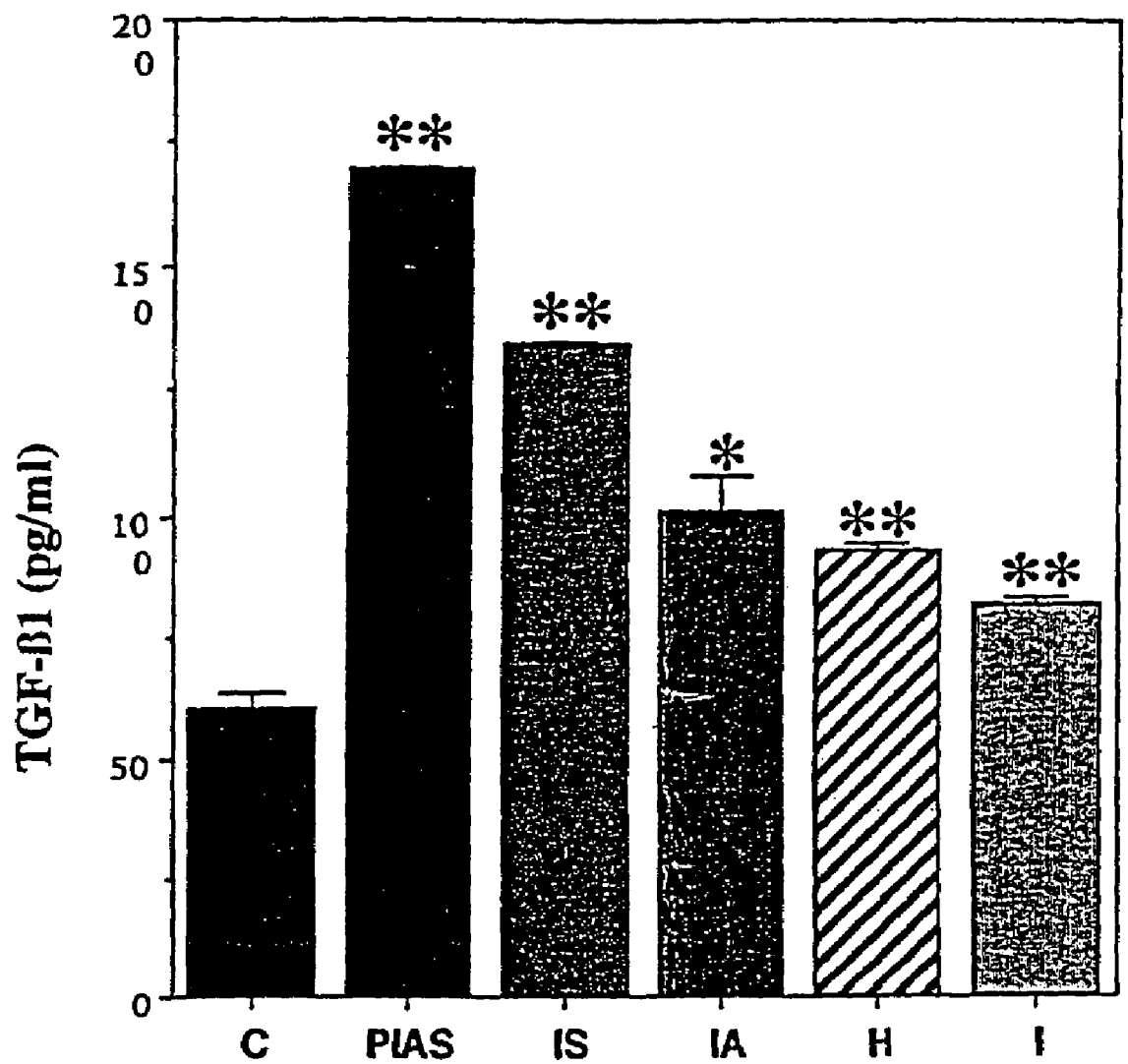
FIG. 7 shows the effect of the unsaponifiable components of avocado and of soya bean and of fractions H and I on the expression of TGF-β1.

Several processes have been described in the prior art for extracting the unsaponifiable fraction of a vegetable oil.

There may be mentioned in particular the process for the preparation of unsaponifiable component of avocado oil as described and claimed in patent FR-2,678,632 in the name of Pharmascience Laboratories. This process makes it possible to obtain an unsaponifiable component of avocado rich in fraction H compared with the conventional processes for the preparation of unsaponifiable component of avocado.

There may also be mentioned the process for the preparation of unsaponifiable component of soya bean oil, obtained from a concentrate of unsaponifiable component of soya bean oil. The said concentrate of unsaponifiable component is prepared by molecular distillation according to a process as described for lupin oil in patent application FR-2,762,512, but adapted to soya bean oil. In this process, the soya bean oil is distilled in a scraped-film or centrifugal type molecular distillator, at a temperature of between about 210 and 250° C. and under a high vacuum, of between 0.01 and 0.001 millimeters of mercury (that is to say 0.13 to 1.3 Pa). The distillate obtained has a content of unsaponifiable component of between 5 and 30% by weight and therefore constitutes a concentrate of unsaponifiable component of soya bean oil. The same concentrate is then saponified according to a conventional saponification process, in the presence of ethanolic potassium hydroxide. The mixture obtained is extracted with dichloroethane in a countercurrent column. The solvent phase is finally freed of solvent by passage through a falling film evaporator in order to recover the unsaponifiable component of soya bean.

As an example of a process for the preparation of unsaponifiable component of lupin oil, there may be mentioned that described in patent application FR-2,762,512. Reference may be made in particular to Example 3 of this application.

According to a preferred embodiment of the present invention, the unsaponifiable component of vegetable oil is a mixture of unsaponifiable components of avocado and soya bean oils, the weight ratio of unsaponifiable component of avocado oil to the unsaponifiable component of soya bean oil being between about 0.1 and about 9, and preferably between about 0.25 and about 0.6.

In particular, it is possible to advantageously use the mixture of unsaponifiable components of avocado and soya bean oils as marketed by the company Pharmascience Laboratories under the name "Piasclédine 300®" which consists of a mixture of 33.3% by weight of unsaponifiable component of avocado and 66.6% by weight of unsaponifiable component of soya bean, relative to the total weight of the mixture (the remaining 0.1% consisting of colloidal silica and butylated hydroxytoluene).

Preferably, the unsaponifiable component of vegetable oil according to the invention is used such that it is present in the medicament in a proportion of between about 1 and about 80% by weight, relative to the total weight of the medicament.

The medicament prepared by the use according to the present invention may thus comprise, in addition, a pharmaceutically acceptable excipient, preferably suitable for administration by the oral, external topical, enteral or parenteral route.

More particularly, this medicament comprises an excipient suitable for administration by the oral route.

The medicament prepared by the use according to the invention, because of its stimulatory action on the expression of TGF-β and its stimulatory action on the expression of the plasminogen activator inhibitor PAI-1, is therefore advantageously intended for the treatments of pathologies for which at least one of these actions is sought.

In particular, the use according to the invention is characterized in that the medicament is intended for the treatment of conditions of the joints, more particularly for the treatment of osteoarthritis and for the treatment of arthritis (that is to say rheumatoid arthritis, psoriatic arthritis, Lyme arthritis and/or any other type of arthritis).

The use according to the invention is also characterized in that the medicament may be intended for the treatment of parodontai conditions, and in particular for the treatment of periodontitis.

The use according to the invention is moreover characterized in that the medicament may be intended for the treatment of osteoporosis.

In addition, the use according to the invention is characterized in that the medicament may be intended for modulating the differentiation of nerve cells induced by NGF. "Modulating" is understood to mean, according to the invention, the action of increasing or decreasing the differentiation of the nerve cells induced by NGF.

Finally, the use according to the invention is characterized in that the medicament may be intended for tissue repair, and in particular for skin tissue repair, in particular in the context of a dermatological application.

Moreover, as illustrated in Example 2, below, the use according to the invention is characterized in that the medicament is intended for stimulating the biosynthesis of collagen, in particular by derma fibroblasts. More particularly, the use according to the invention is characterized in that the medicament is intended for the reconstruction of the extracellular matrix, and is still more particularly intended for the treatment of disorders of the extracellular matrix linked to skin ageing.

The present invention finally also relates to a method of cosmetic treatment of the skin, of the neighbouring mucous membranes and/or of the superficial body growths, characterized in that a cosmetic composition comprising at least one unsaponifiable component of vegetable oil as defined above, and at least one cosmetically acceptable vehicle such as the vehicles generally used in the field of cosmetic products, is applied to the skin, the neighbouring mucous membranes and/or the superficial body growths. Preferably, it involves a method of cosmetic treatment of scars on the skin, of the intrinsic ageing of the skin (that is to say of the ageing of the skin not resulting predominantly from an action external to the skin) and a method of cosmetic treatment of the skin which has been subjected to an actinic ray, in particular to an ultraviolet ray.

Moreover, it is known that TGF-β acts at the level of the hair cycle by modulating hair regrowth in the direction of an inhibition. In addition, according to an as yet poorly elucidated mechanism, it is found that TGF-β exerts an action on the follicular tissues whose effect is to cause hair loss. These two actions are therefore of obvious cosmetic importance in the field of depilation. In particular, the complementary depilatory effects (inhibiting hair regrowth and causing hair loss) advantageously allow the user to have a gap between the more constraining and often more expensive conventional depilation sessions, including mechanical shaving sessions in particular in men. This cosmetic use can for example be envisaged in the form of an after-depilation or aftershave balm combining the conventional cosmetic effects of this type of balm (moisturizing, soothing effect, and the like) and its depilatory effects.

A further subject of the present invention is therefore a method of cosmetic depilatory treatment of the skin, characterized in that a cosmetic composition comprising at least one unsaponifiable component of vegetable oil and at least one cosmetically acceptable vehicle is applied to the skin.

Preferably, the unsaponifiable component of vegetable oil is present in the cosmetic composition in a proportion of between about 0.1 and about 10% by weight, relative to the total weight of the cosmetic composition.

Finally, the present invention relates to the use of at least one unsaponifiable component of vegetable oil as defined above as additive in a food for human beings and/or for animals, the unsaponifiable component of vegetable oil being present in the food in a proportion preferably of between about 0.1 and about 20% by weight, relative to the total weight of the food.

The present invention will now be illustrated with the aid of examples which should in no case be interpreted as being capable of limiting the scope thereof.

EXAMPLE 1

Effect of the Unsaponifiable Components of Avocado and of Soya Bean on the Expression of TGF-β1 and TGF-β2 and on the expression of PAI-1

1.1 Materials and Methods 1.1.1 Culture and Treatment of Articular Chondrocytes

The chondrocytes are isolated from calf cartilages as described in the article by Benya et al. ("The progeny of articular chondrocytes synthesize collagen types I and II trimer, but not type II. Verification by cyanogen bromide peptide analysis", Biochemistry 1977; 16: 865-872). Primary cultures of chondrocytes are used in order to minimize the phenotypic changes. The cultures are plated at the rate of $6.0 \times 10^6$ cells per 175-cm$^2$ dish (for the extraction of RNA), at the rate of $5.0 \times 10^6$ cells per well in 6-well plates (9.6 cm$^2$) (for the labelling of PAI-1) and at the rate of $1.2 \times 10^6$ cells in 100-mm Petri dishes (transfection). The cultures are incubated in complete DMEM medium (DMEM for "Dulbecco's modified Eagle's medium") containing 10% foetal calf serum (FCS) and antibiotics at 35° C. in an atmosphere containing 5% $CO_2$ and 95% air, until confluence is reached (with the exception of the transfection assays). The cultures are incubated in the presence of unsaponifiable components of avocado and of soya bean in the form of the product. "Piasclédine 300®" (marketed by the company Pharmascience Laboratories) which contains 33.3% of unsaponifiable component of avocado oil and 66.6% of unsaponifiable component of soya bean oil. The concentration of Piasclédine 300® being 10 µg/ml, and in the presence of TGF-β1 in an amount of 1 ng/ml (marketed by the company R & D Systems) for the indicated times. Since Piasclédine 300® is dissolved in dimethylformamide (DMF), controls containing the same concentration of DMF are included in all the assays.

1.1.2. Extraction of RNA

The total RNA is extracted by the method of differential solubilization with phenol/chloroform using the commercial kit RNAXe1 from the company Eurobio. The concentrations of RNA are determined by measuring the value of the optical density at 260 nm ($OD_{260}$). The $OD_{260}/OD_{280}$ ratios are greater than 1.8. The integrity of the RNA samples is checked by 1% agarose gel electrophoresis in the presence of ethidium bromide. In the case of a genomic DNA contamination, an additional precipitation with GM lithium chloride LiC1 is carried out in order to obtain pure RNA samples.

1.1.3. Hybridization of RNA (Northern Blotting)

10 µg of denatured RNA samples are run on a 1% formaldehyde-agarose gel. The RNA is transferred by capillarity onto a nylon membrane (Pall Biodyne, Gelman Sciences) and immobilized by irradiation with ultraviolet radiation (Bioblock UV Crosslinker, France). Three different probes are used to evaluate the mRNA values for TGF-β, PAI-1, β-actin: (a) there is generated a 336 base pair (bp) cDNA probe for TGF-β1 by RT-PCR (reverse transcription and polymerase chain reaction) using the primers indicated below, (b) a 3000 bp cDNA fragment corresponding to human PAI-1 (provided by the laboratory of Dr J-P Pelletier, Montreal, Canada) and (c) a 548 bp probe for β-actin generated by RT-PCR with the specific primers listed below. The cDNA probes are radiolabelled using the kit for random labelling of the primers (Gibco BRL, France) and [$^{32}$P]-dCTP as radiolabel (Amersham, France). Each probe is hybridized separately at 55° C. and washed twice for 20 minutes at room temperature and once at 55° C. with a 2×SSC buffer containing 0.1% SDS. The signals are detected by film contact autoradiography using a Kodak film (X-OMAT AR5) with intensifying screens. The relative optical density of the autoradiographic signals is normalized with respect to the values for β-actin using the two-dimensional laser scanning derisiometry technique and the ImageQuaNt software (Molecular Dynamics, France).

1.1.4. RT-PCR Analysis

1-µg samples of total RNA are reverse-transcribed into cDNA in the presence of a 100 pM antisense primer, 10 units of "RNasin®" (a ribonuclease inhibitor marketed by the company Promega), 10 mM dithiothreitol, 0.5 mM of each deoxynucleotide triphosphate (dNTPs) (Life Technologies), a first 5× "Strand" buffer and 60 units of Moloney murine leukaemia virus reverse transcriptase (Life Technologies). The reaction is carried out at 42° C. for one hour. The amplification of the cDNA generated is carried out in an Omni E Hybaid thermocycler using the PCR kit from Life Technologies, in the presence of sense and antisense primers: TGF-β1, sense 5'-GCC CTG GAC ACC AAC TAT TGC-3'/antisense 5'-GCT GCA CTT GCA GGA GGG CAC-3' (Lupparello et al., "Transforming Growth Factor-β1, -β2 and -β3, urokinase and parathyroid hormone-related peptide expression in 8701-Bc breast cancer cell and clones", Differentiation, 1993; 55: 73-80); TβR-I, sense 5'-ATT GCT GGA CCA GTG TGC TTC GTC-3'/antisense 5'-TAA GTC TGC AAT ACA GCA AGT TCC ATT CTT-3' (Franzen et al.), "Cloning of TGF-β type I receptor that forms a heteromeric complex with the TGF-β type II receptor" Cell, 1992; 75: 681-692); TβR-II, sense 5'-CGC TTT GCT GAG GTC TAT AAG GCC 3'/antisense 5'-GAT ATT GGA GCT CTT GAG GTC CCT-3' (Lin Hy et al., "Expression cloning of the TGF-β type II receptor, a functional transmembrane serine/threonine kinase" Cell, 1992; 68: 775-785); β-actin, sense 5'-GTG GGG CGC CCC AGG CAC CA3'/antisense 5'-CTC CTT AAT GTC ACG CAC GAT TTC-3' (Lupparello et al., reference cited above). 35 cycles were carried out using the following conditions: 95° C. for 30 seconds, 55° C. for 30 seconds and 72° C. for 1 minute. Next, an additional step at 72° C. for 10 minutes is included. The number of cycles is chosen in the exponential phase of the amplification curve previously established. The transcripts were analysed by electrophoresis on a 2% agarose gel and visualized by staining with ethidium bromide. The amplification reactions provided expected sizes of transcript TGF-β1 336 bp, TβR-I: 668 bp, TβR-II: 454 bp, β-actin: 548 bp. The identity of PCR products is also confirmed by restriction endonuclease digestion and by Southern-blotting, using the respective human probes which correspond, for TβR-I and Tβ-II, to the total length of the cDNAs and for TGF-β1, β-actin to the fragments generated by RT-PCR. After photography of the gels with a polaroid 665 film, the intensity of the corresponding bands is quantified by densiometric scanning carried out with the ImageQuaNt software (Molecular Dynamics) and normalized with respect to the β-actin mRNA values.

1.1.5. Measurement of the Secreted Mature TGF-β1

In order to measure the quantity of active TGF-β1 in the medium conditioned by the control cells or the cells treated with the unsaponifiable components of avocado and of soya bean, the confluent monolayer cells in the 6-well culture plates are incubated for 24 hours in the medium containing 10% FCS, with or without 10 µg of Piasclédine 300®. The cells are washed three times with a serum-free medium supplemented with 200 µg/ml of BSA (bovine serum albumin) for 5, 30 and 60 minutes, and incubated in 1 ml of serum-free medium for an additional 6 hours. The conditioned medium is then collected in silicone tubes for microcentrifugation, centrifuged and the quantity of activated, mature TGF-β1 is determined in the supernatant by immunoassay of TGF-β1 using the Quantikine® kit (Quantikine® R&D Systems, U.S.A.) according to the manufacturer's instructions.

1.1.6. Radiolabelling for the Synthesis of PAI-1

The confluent cultures in 6-well plates (9.6 cm$^2$) are labelled with [$^{35}$S]methionine (40 µCi/nil, Arnersham, France) in the presence of Piasclédine 300® (10 µg/ml) and TGF-β1 (1 ng/ml) for 24 hours. The extraction of the radiolabelled proteins and the characterization of PAI-1 by electrophoresis are carried out as described in the article by Laiho M et al. "Transforming Growth Factor-β induction of type-1 plasminogen activator inhibitor" J. Biol. Chem. 1987; 262: 17467-17474) with a few modifications. Briefly, the media are removed and the layers of cells are scraped off into 1 ml of 10 mM Tris-HC1 buffer at pH 8, containing 0.5% sodium deoxycholate and 1 mM phenylmethylsulphonyl fluoride. The samples are centrifuged at 4° C. and 10,000 g for 10 minutes. The supernatants are absorbed with concariavalin A (Con A)-Sepharose (Pharmacia) (50 pl of 50% (v/v) suspension in PBS). The Con A-Sepharose is washed three times with a PBS/Tween 80 (0.01%) mixture and the bound proteins are dissolved in Laemmli buffer (Laemmli et al., "Cleavage of structural proteins during the assembly of the head of bacteriophage T$_4$" Nature, 1970; 227: 680-685) containing 10% 2-mercaptoethanol. The proteins bound on concanavalin A are subjected to electrophoresis on a 10% polyacrylamide gel in the presence of sodium dodecyl sulphate-polyacrylamide (SDS-PAGE) followed by fluorography. Ovalbumin (M 46,000) and carbonic anhydrase (M$_r$ 29,000) are used as molecular weight marker. The band at 46 kD is determined to correspond to PAI-1 by previous immunoblotting using a rabbit polyclonal anti-PAI-1 antibody (Dako, Copenhagen, Denmark) as described in the article by Laiho M et al., reference cited above.

1.1.7. Cell Transfection and Assay of Luciferase Activity

For the transient transfections, the cells are 25 plated on 100-mm Petri dishes and they are grown to 70-80% confluence. The cells are then cotransfected by the calcium phosphate coprecipitation method (Bradford et al., "A rapid and sensitive method for the quantification of microgram quantities of protein utilizing the principle of protein-dye binding", Anal. Biochem, 1976; 72: 248-254), with 9 µg of appropriate plasmids and 3 µg of pSV40-β Gal (Promega), a β-galactosidase expression vector used as internal standard to normalize the transfection efficiency. After 24 hours, the medium is replaced with a medium containing DMF (1:1000) in the absence or in the presence of Piasclédine 300® (10 µg/ml).

The cells are harvested 48 hours after the addition of DNA and the extracts are tested for the luciferase activity. Briefly, the Petri dishes are washed twice with PBS, and the cells are lysed with 300 µl of lysis buffer (0.45 mM Tris-HC1, pH 7.5). The lysates are subjected to three freeze-thaw cycles. After centrifugation, the luminescence in an aliquot of 50 µl of lysate from each Petri dish is measured in a luminometer (Berthold Lumat 9501) for 20 seconds after addition of luciferin (Luciferase Assay System, company Promega). To normalize the luciferase activity, the protein concentration and the β-galactosidase activity are determined. The protein concentration of the cell lysates of 4 µl from each Petri dish is measured according to Bradford as cited in the reference above. The cell lysates are tested for the β-galactosidase activity using the resofurine β-D-galactopiranoside as substrates and the OD is measured at 572 nm.

1.1.8. Construction of the Plasmids

The constructs containing the TGF-βI promoter are generated from the plasmid phTG2 (Kim et al., "Characterization of the promoter region of the human transforming growth factor-β1 gene", J. Biol. Chem. 1989; 264: 402-408) provided by Dr S. J. Kim (Laboratory for Chemoprevention, NIH/NCI; Bethesda). The digestion of the plasmid phTG2 with the enzymes HindIII and XlaI respectively generates DNA fragments corresponding to the respective promoter sequences −1132 to +11 and −732 to +11. After filling the cohesive ends with the Klenow fragment, the DNA fragments are digested with KpnI and are then cloned into the standard reporter plasmid pGL2 at the SmaI/KpnI site (Promega) encoding the gene for luciferase without a promoter sequence. The construct containing the promoter region −454/+11 corresponds to the cloning of a DNA sequence obtained by digesting phTG2 with HindII- and KpnI into an SmaI-KpnI site of the standard reporter plasmid pGL2.

2. Results 2.1. Effect of the Unsaponifiable Components of Avocado and of Soya Bean (Piasclédine 300®) on the Expression of TGF-β1 and TGF-β2

The effect of Piasclédine 300® on bovine articular chondrocytes is determined in confluent primary cultures incubated for 24 hours in the presence or in the absence of Piasclédine 300® (10 pg/ml), the controls containing the same concentration of dimethylformamide (DMF 1:1000) which is used as solvent for the extract. No morphological change or cell detachment was observed with concentrations up to 100 µg/ml, as examined by phase contrast microscopy. However, the concentration of 10 µg/ml was selected for most of the assays since the DMF value in the samples at 100 µg/ml would have been too high and potentially harmful to the cells. The expression of TGF-β1 and TGF-β2 was determined after extraction of total RNA by northern blotting.

As shown in FIG. 1, the treatment of BAC (Bovine Articular Chondrocytes) with Piasclédine 300® at 10 µg/ml caused a notable increase in the level of TGF-β1 mRNA compared with the controls, when the message was hardly detectable. Two transcripts of 1.9 and 2.4 kb were observed on the northern-blots. This increased expression of the TGF-β1 gene induced by Piasclédine 300® is specific since the expression of the mRNA for β-actin which corresponds to a housekeeping gene did not significantly change under the same experimental conditions.

To determine if this transcription effect is accompanied by an increase in the synthesis of the TGF-β3 proteins, an ELISA assay makes it possible to estimate the concentration of TGF-β1 released into the Piasclédine 300®-treated cell culture mediua. FIG. 1 shows that the production of immunodetectable TGF-β1 is increased by a 24-hour exposure to Piasclédine 300® 10 µg/ml. Although the assay does not make it possible to distinguish the latent TGF-β from the activated TGF-β, it is clearly evident that a correlation exists between the effect of the unsaponifiable components of avocado and of soya bean on the transcription and the translation and on the expression of TGF-β1.

In a second series of experiments, the effects of Piascledine 300® on the level of expression both of TGF-β1 and of TGF-β2 in the presence or in the absence of exogenous TGF-β1 was examined. As shown in FIG. 2, the expression of TGF-β2 was also stimulated by Piascledine 300®. Interestingly, in the case of TGF-β1, a synergistic effect was observed, showing that amplification loops may occur in the system.

2.2. Effect (Time- and Dose-Dependence) of the Unsaponifiable Components of Avocado and of Soya Bean on the Expression of TGF-β1 as a Function of the Time and of the Doses Since these results show that Piascledine 300® 20 induces an increase in the expression of TGF-β1, it was desired to determine the effects of different concentrations of unsaponifiable components of avocado and of soya bean and of the different incubation times on the level of expression of the mRNAs for TGF-β1. Since the signal detected by the northern-blot method is relatively weak for the untreated control chondrocytes (see FIG. 1), the use of the RT-PCR method is preferred for carrying out these assays. The treatment of chondrocytes with Piascledine 300® at increasing concentrations (5, 10 and 25 µg/ml) makes it possible to observe a response to stimulation for Piascledine 300® concentrations of 10 and 25 µg/ml with a greater effect for a concentration of 10 µg/ml. The concentration of 5 µg/ml is probably too low to produce any effect (see FIG. 3). The treatment of chondrocytes with Piascledine 300® at a concentration of 10 µg/ml for periods of 12, 24 or 48 hours, makes it possible to observe an increase in the level of expression of the mRNAs for TGF-β1 at all the incubation times with a maximum at 48 hours (see FIG. 3).

2.3. Effect of the Unsaponifiable Components of Avocado and of Soya Bean on the Cellular Expression Directed by the Flanking 5' Region of the TGF-β1 Gene According to the preceding results which show that the unsaponifiable components of avocado and of soya bean can stimulate the transcription activity of the promoter of the TGF-β1 gene, the aim of this assay is to delimit the sequences in cis of the TGF-β1 gene which are capable of mediating this effect. A series of fragments of the 5'-region of the promoter of the human TGF-β1 gene, fused with the luciferase gene, are transfected into bovine chondrocytes and then treated for 24 hours with Piascledine 300® at 10 µg/ml. The expression of the luciferase activity is then tested for each plasmid. As shown in FIG. 4, the longest construct used (−1132 to +11) induces an expression of luciferase activity which is 8 times higher than that for the control. The other sequences corresponding to the most downstream region (−732 to +11) produce no significant change as regards the expression of luciferase compared with that for the controls.

These results show that the DNA sequences responding to the stimulation of the unsaponifiable components of avocado and of soya bean on the expression of the TGF-β1 gene are situated between −1132 and −732.

2.4. Effect of the Unsaponifiable Components of Avocado and of Soya Bean on the Expression of the Receptors for TGF-β

Since the biological activity of TGF-β is mediated via its binding to the cell membrane receptors, it was proposed to study the effects of the unsaponifiable components of avocado and of soya bean on the expression of the receptors for TGF-β by measuring the corresponding levels of mRNA. As shown in FIG. 5, the treatment with Piascledine 300® induces no variation in the level of expression of the mRNAs for TβR-I and for TβR-II. Analysis of these data by densitometric scanning and normalization with respect to the signal for β-actin shows that the relative ratio for TβR-I established with the amplification at 35 cycles is 1.16 in the treated cultures compared with the value of 1.23 in the controls and the value of 0.83 for TβR-II in relation to 0.70 in the controls.

2.5. Effect of the Unsaponifiable Components of Avocado and of Soya Bean on the Expression of PAI-1

In the confluent monolayer cultures of the chondrocytes used in these assays, previous assays showed that the PAI-1 produced by the cells was essentially found in the layer of cell, which comprises an abundant surrounding matrix. It was observed that the medium contained only minor quantities of newly-synthesized PAI-1. Consequently, $^{35}$S-methionine-labelled PAI-1 was extracted from the cell + matrix fraction without distinguishing between the intracellular part and the extracellular part of the total PAI-1 produced. As shown in FIG. 6, when cultures of bovine chondrocytes were treated with TGF-β1 for 24 hours, the PAI-1 fraction isolated by gel electrophoresis was significantly greater than that for the control cultures. This result provided proof that the cells responded to TGF-β1 in terms of expression of PAI-1 and validated the system used to determine the effect of the unsaponifiable components of avocado and of soya bean. Under the same conditions, it is clear that the avocado and soya bean extracts were able to enhance the synthesis of PAI-1 practically to the same degree as did TGF-β1 (see FIG. 6).

To determine if the stimulatory effect of the unsaponifiable components of soya bean and of avocado on the synthesis of PAI-I is exerted at the transcriptional level, a northern blotting was carried out starting with total RNA isolated from cultures treated in the same manner as for the labelling of the PAI-1 protein. Hybridization with the cDNA probe for PAI-1 labelled with phosphorus-32 demonstrated that the quantity of mRNA encoding PAI-1 is increased during the 24 hours of treatment with the unsaponifiable components of avocado and of soya bean, revealing the correlation existing between the level of expression of mRNA and the protein level (see FIG. 6). It is thus suggested that the unsaponifiable components of avocado and of soya bean are capable of enhancing the synthesis of PAI-1 at the transcriptional level.

EXAMPLE 2

Effect of the Unsaponifiable Components of
Avocado and of Soya Bean and of Fractions H and I
on the Expression of TGF-β1 and on the
Biosynthesis of Collagen by Dermal Fibroblasts in
Culture The cells used for this study are human fibroblasts derived from the foreskin of young children. They were obtained by the technique of explants and cultured in DMEM ("Dulbecco's Modified Eagle Medium") supplemented with 10% foetal calf serum (FCS). The cultures are maintained in a 5% CO2 incubator, at 37° C., and the medium is changed every three days.

1. Effect of the Unsaponifiable Components of Avocado and of Soya Bean and of Fractions H and I on the Expression of TGF-β1

1.1 Experimental Protocol

Human dermal fibroblasts were inoculated into 9.6 cm$^2$ six-well dishes into DMEM supplemented with 10% foetal calf serum (FCS) (3 ml). At confluence, the fibroblast cultures were preincubated with DMEM+2% FCS for 24 hours. The incubation itself is carried out in DMEM+0% FCS in order to avoid the TGF-β present in the serum interfering with the assay. This medium is supplemented with 1.5 ml of the various preparations tested, namely a control (C), Piascledine 300® (PIAS), an unsaponifiable component of soya bean (IS), an unsaponifiable component of avocado (IA) and its fractions enriched with furan derivatives (H) and with polyhydroxylated fatty alcohols (I). The assay is carried out using an ELISA kit (R&D systems).

1.2. Results

The assay of TGF-β1 is carried out on the culture medium according to the supplier's instructions. A calibration series is prepared using known quantities of TGF-β1, which makes it possible to draw a straight line for the optical density (OD) with respect to the concentration and to determine the equation of the straight line as well as the correlation coefficient. The concentration of TGF-β1 in our samples is calculated using the OD values obtained with the various preparations tested. The results are expressed in pg/ml of TGF-β1 and represent the mean for 3 samples.

These results presented in FIG. 7 show that PIAS, IS, IA, H and I stimulate the production of TGF-β1 by the dermal fibroblasts in culture.

2. Effect of the Unsaponifiable Components of Avocado and of Soya Bean and of Fractions H and I on the Biosynthesis of Collagen by Dermal Fibroblasts in Culture 2.1. Experimental Protocol Confluent cultures of dermal fibroblasts (6 wells of 9.6 cm$^2$) are preincubated with ascorbic acid (3 ml). After 24 hours, the medium is replaced with 1.5 ml of (DMEM/10% FCS medium supplemented with β/APN (aminopropionitrile), ascorbic acid and $^3$H-Proline(2 µCi/ml).

The biosynthesis of collagen was measured by the assay technique using purified bacterial collagenase described by Peterkofsky and Diegelmann (1971).

24 h after treating the cultures with the various preparations tested, namely a control (C), Piascledine 300® (PIAS), an unsaponifiable component of soya bean (IS), an unsaponifiable component of avocado (IA) and its fractions enriched with furan derivatives (H) and with polyhydroxylated fatty alcohols (I), at 20 µg/ml (solubilized beforehand in absolute ethanol), the assay is carried out on the culture medium because, in the presence of aminopropionitrile, most of the collagen synthesized (95%) by the fibroblasts in culture is present in soluble form.

2.2 Results

The results are presented in FIGS. 8A and 8B. As shown in FIG. 8A, the preparations PIAS, IS, IA, H and I increase the biosynthesis of collagen by the human dermal fibroblasts for concentrations of 20 µg/ml.

The effects observed are specific to collagens since there is no effect on the biosynthesis of noncollagenic proteins, as shown in FIG. 8B.

All these results show that the substances PIAS, IS, IA, H and I stimulate the biosynthesis of collagen by the dermal fibroblasts in culture.

3. Conclusion

The results of this study show that the unsaponifiable components of avocado and of soya bean (PIAS, IS, IA, H and I) stimulate the biosynthesis of collagen by dermal fibroblasts in culture. Furthermore, these effects are specific to collagen since there is no effect on the biosynthesis of the noncollagenic proteins.

Moreover, the preparations used increase the production of TGF-β1 by the dermal fibroblasts.

The latter result indicates that the stimulation of the biosynthesis of collagen by the different preparations would require a pathway involving TGF-β1.

The results obtained in this study show that the unsaponifiable components of avocado and soya bean (PIAS, IS, IA, H and I) are capable of increasing the biosynthesis of collagen, the principal molecule of the extracellular matrix (ECM) produced by the dermal fibroblasts. Furthermore, these preparations increase the production of TGF-β1, a potent stimulant of the synthesis of the principal macromolecules of the ECM.

The unsaponifiable components of avocado and soya bean, through their action on the biosynthesis of collagen and of TGF-β1, therefore exhibit great potential for the reconstruction of the ECM, in particular in the phenomenon of skin ageing.

What is claimed is:

1. A cosmetic composition for skin comprising:
   at least one unsaponifiable component from avocado oil;
   at least one unsaponifiable component from soya bean oil, lupin oil, or mixtures thereof; and
   at least one cosmetically acceptable vehicle for applying the composition to skin,
   wherein the at least one unsaponifiable component from avocado oil is chosen from dry avocado oils,
   wherein the unsaponifiable component from soya bean oil, lupin oil, or mixtures thereof comprises about 40% to about 65% sterols and greater than about 10% tocopherols,
   wherein the cosmetic composition has a weight ratio of the unsaponifiable component from avocado oil to the unsaponifiable component from soya bean oil, lupin oil, or mixtures thereof of about 0.1 to about 9, and
   wherein the unsaponifiable component from avocado oil and the unsaponifiable component from soya bean oil, lupin oil, or mixtures thereof comprise about 0.1% to about 10% of the composition by weight.

2. A cosmetic treatment for scars comprising applying a composition to skin, neighboring mucous membranes, superficial body growths, or a combination thereof, wherein the composition comprises
   at least one unsaponifiable component from avocado oil;
   at least one unsaponifiable component from soya bean oil, lupin oil, or mixtures thereof; and
   at least one cosmetically acceptable vehicle for applying the composition to skin.

3. A method for treating a scar comprising applying to the skin, neighboring mucous membrane, and/or superficial body growth of a patient in need thereof an effective amount of a composition comprising:
   at least one unsaponifiable component from avocado oil;
   at least one unsaponifiable component from soya bean oil, lupin oil, or a mixture thereof; and
   at least one cosmetically acceptable vehicle for applying the composition.

4. A method for treating hirsute skin comprising applying to the skin of a patient in need thereof an effective amount of a composition comprising:
   at least one unsaponifiable component from avocado oil;
   at least one unsaponifiable component from soya bean oil, lupin oil, or a mixture thereof; and at least one cosmetically acceptable vehicle for applying the composition.

5. The method of claim 3 or 4, wherein the composition comprises at least one unsaponifiable component from dry bean oil.

6. The method of claim 3 or 4, wherein the composition comprises at least one unsaponifiable component from soya bean oil.

7. The method of claim 3 or 4, wherein the at least one unsaponifiable component from avocado oil comprises at least one fraction enriched with furan derivatives, at least one fraction enriched with polyhydroxylated fatty alcohols, or a mixture thereof.

8. The method of claim 3 or 4, wherein the at least one unsaponifiable component from soya bean oil, lupin oil, or a mixture thereof is mainly composed of sterols and tocopherols.

9. The method of claim 3 or 4, wherein the at least one unsaponifiable component from soya bean oil, lupin oil, or a mixture thereof comprises from about 40% to about 65% sterols and greater than about 10% tocopherols.

10. The method of claim 3 or 4, wherein the composition has a weight ratio of the at least one unsaponifiable component from avocado oil to the at least one unsaponifiable component from soya bean oil, lupin oil, or a mixture thereof ranging from about 0.1 to about 9.

11. The method of claim 3 or 4, wherein at least one unsaponifiable component comprises a fraction rich in phytosterols, tocopherols, tocotrienols, terpenic and triterpenic hydrocarbons, natural antioxidants, or a mixture thereof.

12. The method of claim 3 or 4, wherein the at least one unsaponifiable component from avocado oil and the at least one unsaponifiable component from soya bean oil, lupin oil, or a mixture thereof comprise from about 0.1% to about 10% of the composition by weight.

13. The method of claim 3 or 4, wherein the at least one unsaponifiable component from avocado oil and the at least one unsaponifiable component from soya bean oil comprise from about 0.1% to about 10% of the composition by weight.

14. The method of claim 3 or 4, wherein the composition further comprises at least one unsaponifiable component from canola oil, rapeseed oil, sunflower oil, palm oil, maize oil, sesame oil, wheatgerm oil, or a mixture thereof.

15. A method for a treating scar comprising applying to the skin, neighboring mucous membrane, and/or superficial body growth of a patient in need thereof an effective amount of a composition comprising:
   at least one unsaponifiable component from canola oil, rapeseed oil, sunflower oil, palm oil, maize oil, sesame oil, wheatgerm oil, or a mixture thereof;
   at least one unsaponifiable component from avocado oil, lupin, soya bean oil, or a mixture thereof; and
   at least one cosmetically acceptable vehicle for applying the composition.

16. A method for treating hirsute skin comprising applying to the skin of a patient in need thereof an effective amount of a composition comprising:
   at least one unsaponifiable component from canola oil, rapeseed oil, sunflower oil, palm oil, maize oil, sesame oil, wheatgerm oil, or a mixture thereof;
   at least one unsaponifiable component from avocado oil, lupin, soya bean oil, or a mixture thereof; and
   at least one cosmetically acceptable vehicle for applying the composition.

17. The method of claim 15 or 16, wherein the at least one unsaponifiable component from canola oil, rapeseed oil, sunflower oil, palm oil, maize oil, sesame oil, wheatgerm oil, or a mixture thereof, and the at least one unsaponifiable component from avocado oil, lupin oil, soya oil or a mixture thereof comprise from about 0.1% to about 10% of the composition by weight.

* * * * *